United States Patent [19]
Martinez

[11] 3,944,342
[45] Mar. 16, 1976

[54] PHOTOGRAPHIC APPARATUS FOR SLIT LAMP

[75] Inventor: Miguel Martinez, Baltimore, Md.

[73] Assignee: Codman & Shurtleff, Inc., Randolph, Mass.

[22] Filed: Apr. 30, 1974

[21] Appl. No.: 465,589

[52] U.S. Cl. .................. 351/14; 350/19; 351/7; 354/79
[51] Int. Cl.² .................................... A61B 3/14
[58] Field of Search .......... 351/14, 7, 19, 6; 354/79; 350/19

[56] References Cited
UNITED STATES PATENTS

| | | | |
|---|---|---|---|
| 2,290,874 | 7/1942 | Graff | 354/79 |
| 2,933,992 | 4/1960 | Bushnell et al. | 350/19 X |
| 3,652,153 | 3/1972 | Gambs | 351/14 |
| 3,830,562 | 8/1974 | McGrann et al. | 351/14 |

*Primary Examiner*—Paul A. Sacher
*Attorney, Agent, or Firm*—John J. Simkanich

[57] ABSTRACT

Photographic apparatus for a slit lamp includes a photographic camera adapted to be mounted on one ocular of a binocular microscope of the slit lamp and a light sensing device positioned adjacent an objective of the microscope for providing a signal corresponding to light at the objective to an automatic exposure control mechanism in the camera, the other ocular of the microscope being free to permit viewing of an object being photographed.

20 Claims, 10 Drawing Figures

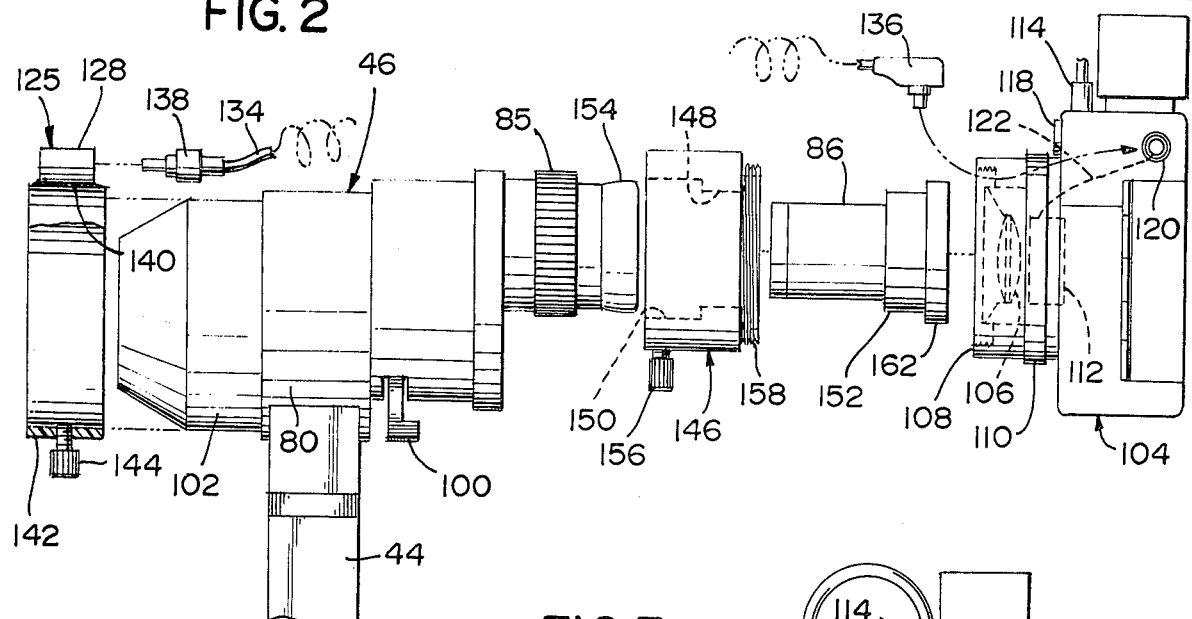
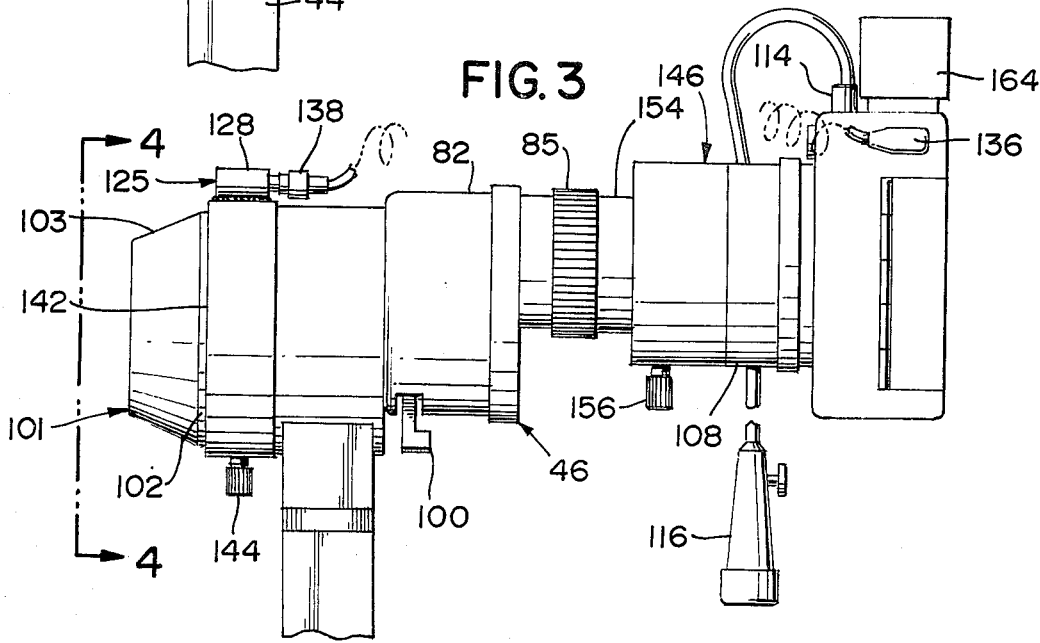
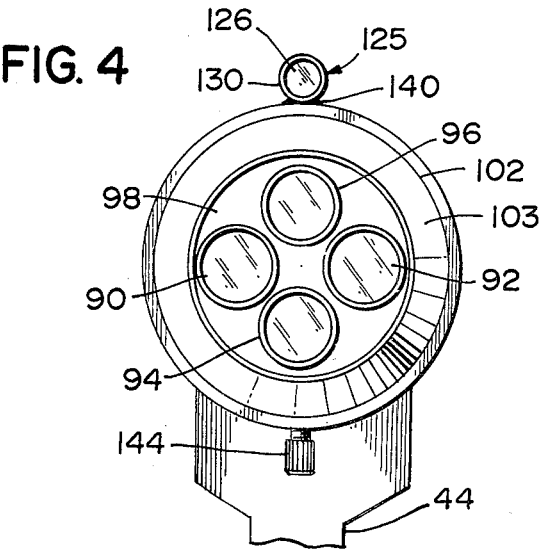
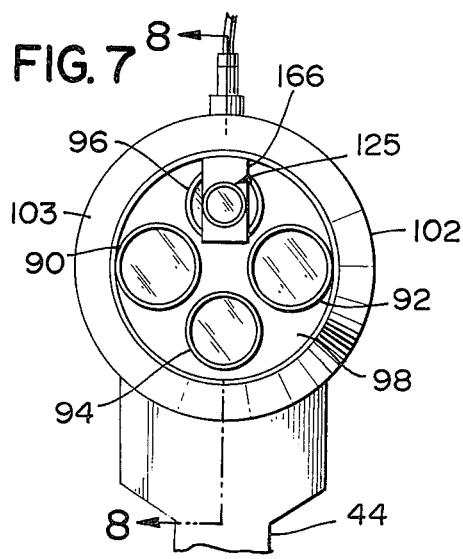

PHOTOGRAPHIC APPARATUS FOR SLIT LAMP

BACKGROUND OF THE INVENTION

1. Field of the Invention

The present invention pertains to photographing objects through an optical image-enlarging instrument and, more particularly, to photographing the human eye through the microscope of a slit lamp.

2. Discussion of the Prior Art

Slit Lamps are conventionally utilized by opthalmologists to examine the human eye by projecting a slit of light into the eye of a subject through an optical system. The optical system includes various optical components for controlling the configuration and size of the light beam as well as circuitry to control the intensity of the lamp. The opthalmologist examines the eye of the subject illuminated by the light beam through a microscope mounted adjacent the optical system, and it is frequently desirable for the opthalmologist to record the image of the eye viewed through the microscope for various reasons, such as to provide a record of the progress of a disease, deterioration of a part of the eye or treatment of the eye. In the past, the opthalmologist has recorded the images of the eye by sketching the image by hand, this method having many obvious disadvantages including being inaccurate and time consuming.

In order to facilitate the recording of images of an eye being examined, slit lamps have been modified to permit photographs of the eye to be obtained. Such modified slit lamps, as exemplified by U.S. Pat. Nos. 3,519,338; 3,591,262; 3,652,153; and 3,762,803 have had one or more of the disadvantages of the photographic apparatus being integrally combined with the slit lamp and, therefore, increasing cost and complexity of the modified slit lamp while reducing flexibility and universal use with various types of slit lamps, of requiring an additional light source to provide a flash of light through the optical components to the eye, of dividing the light along the observation axis to provide both viewing and photographing beams, of not photographing the same image viewed by the opthalmologist through the microscope and of requiring additional optical components to enlarge the image of the eye and direct the image to a photographic film.

It has been proposed, as exemplified by U.S. Pat. No. 3,292,490, to take photographs of an image viewed through a binocular microscope by using a camera mounted on one ocular of the microscope having an automatic shutter operated in response to light at the other ocular; however, since both oculars are occupied, the operator cannot view the object to be photographed simultaneously with the actual photographing process. Thus, the object to be photographed must be properly positioned or otherwise placed in a desirable condition for photographing by viewing through one of the oculars of the microscope; and, thereafter, the operator must mount the light sensing attachment on the ocular prior to operating the shutter of the camera. This operation is both cumbersome and time consuming and, furthermore, prevents the operator from detecting movement or other change of the object during the interim between positioning of the object and taking of the photograph.

SUMMARY OF THE INVENTION

The present invention is generally summarized in apparatus for photographing an object through a microscope having an ocular and an objective including a photographic camera having an automatic exposure control mechanism, an adapter for mounting the photographic camera on the ocular of the microscope, a light sensing device for providing a signal representative of light sensed thereby, means for coupling the signal from the light sensing device to the automatic exposure control mechanism to control operation thereof, and means for mounting the light sensing device adjacent the objective of the microscope whereby the automatic exposure control mechanism is operated in response to light at the objective of the microscope.

Accordingly, it is a primary object of the present invention to overcome the above described disadvantages of the prior art by providing apparatus for photographing an object through an ocular of a microscope.

More particularly, it is an object of the present invention to enable an opthalmologist to photograph an eye being examined with a slit lamp in a simple, expeditious manner without requiring expensive modifications of the slit lamp.

Another object of the present invention is to provide photographic apparatus for use with existing slit lamps to permit photographic records of an eye to be taken through one ocular of a binocular microscope while the eye can be viewed through the other ocular of the microscope.

A further object of the present invention is to permit photographing of an eye examined with a slit lamp without requiring an auxiliary flash light source.

The present invention has an additional object in that a conventional 35 mm. automatic exposure camera can be utilized to photograph objects examined with a slit lamp without requiring manual adjustment by mounting a light sensing photoelectric cell adjacent an objective of a microscope of the slit lamp.

Yet another object of the present invention is to utilize the optical system of a binocular microscope to provide an image to be photographed with a camera without requiring that light through the microscope be sensed to provide automatic control of the camera.

The present invention has a further object in the use of the fixation light conventionally provided with slit lamps to provide background illumination for photographs.

An additional object of the present invention is to reduce the light transmitted to a photoelectric cell positioned adjacent an objective of a microscope by mounting a neutraldensity filter in front of the photoelectric cell.

Some of the advantages of the present invention over the prior art are that the photographic apparatus can be easily installed on a slit lamp without requiring technical expertise, no camera adjustments are required prior to the taking of a photograph, all features of the human eye can be clearly and accurately photographed including the external portions, the lens and the anterior and posterior segments, and the photographic apparatus is relatively inexpensive while being usable with various types of slit lamps.

Other objects and advantages of the present invention will become apparent from the following description of the preferred embodiment taken in conjunction with the accompanying drawings.

BRIEF DESCRIPTION OF THE DRAWINGS

FIG. 2 is an exploded side elevation of the slit lamp microscope and the photographic apparatus of the present invention.

FIG. 3 is a side elevation of the photographic apparatus of the present invention mounted on the slit lamp microscope.

FIG. 4 is a front elevation taken along line 4—4 of FIG. 3.

FIG. 7 is a front elevation of a modification of the photographic apparatus of the present invention.

DESCRIPTION OF THE PREFERRED EMBODIMENT

Figure 1:
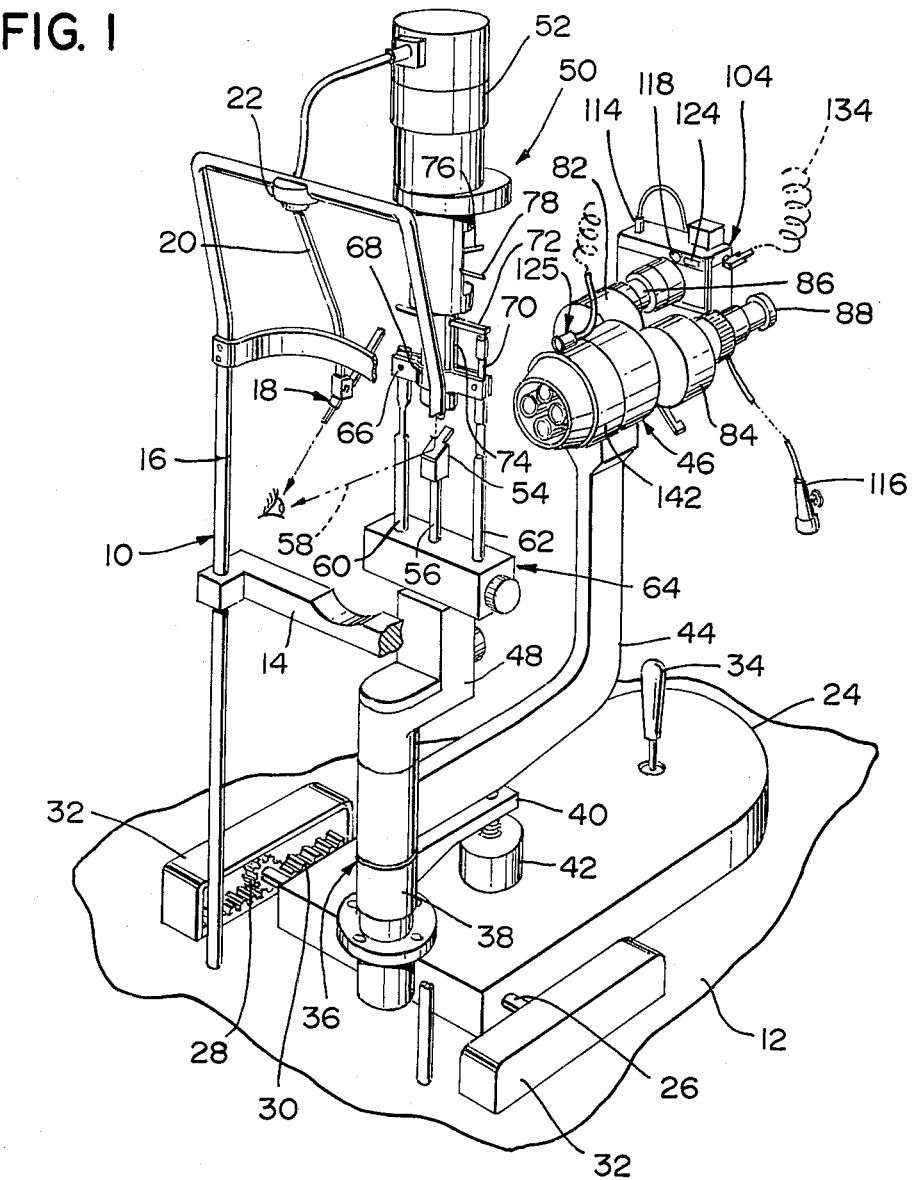
FIG. 1 is a perspective of a slit lamp utilizing photographic apparatus according to the present invention.

A slit lamp utilizing photographic apparatus according to the present invention is illustrated in FIG. 1 and includes a head rest frame 10 mounted on a table 12 or other suitable support with a chin support 14 extending between parallel uprights of the frame 10 and vertically adjustable to permit alignment of a patient's eye level with an eye guide marker 16 on the head rest frame. A fixation light 18 is pivotally mounted on an arm 20 which extends from a rotatable support 22 carried on the top of the head rest frame such that the fixation light can be removed in an arc about the head of a patient. A carriage 24 is mounted to be movable along the table 12 relative to the head rest frame 10 by means of a spherical element, not shown, mounted in the carriage and riding on the surface of the table, the carriage 24 being slidable along a rod 26 carrying pinions 28 at its ends riding on parallel racks 30 formed in housings 32 mounted on the table. A control lever 34 extends from the carriage 24 to be moved by an operator to provide horizontal movement and fine focus of the slit lamp.

Mounted on the carriage 24 is a pivot assembly 36 including a hub 38 having an arm 40 extending transversely therefrom and cooperating with a vertical adjustment knob 42 for raising and lowering the pivot assembly. The pivot assembly 36 includes a microscope arm 44 carrying a binocular microscope 46 and an illumination arm 48 carrying an illumination column 50, the arms 44 and 48 being pivotally mounted on a common vertical pivot pin, not shown, supported by hub 38 such that the microscope 46 and the illumination column 50 are pivotal about the same axis.

The illumination column 50 includes a lamp, not shown, mounted in a housing 52 and arranged to direct a vertical beam of light through a condenser assembly, now shown, to a mirror 54 disposed at the bottom of the illumination column 50 on a post 56 in substantially horizontal alignment with the observation axis of the microscope 46 and oriented at substantially 45° to direct the light beam toward the eye of a patient, as shown at 58. The illumination column 50 is supported on the illumination arm 48 by a pair of spaced columns 60 and 62 extending on opposite sides of mirror 54 between a combination control device 64 and a pair of ears 66 extending from a collar 68, and the post 56 is similarly supported on the combination control device 64. Column 62 has a central bore therein for slidably receiving a control rod 70 having an end abutting a flange 72 extending from a slidable sleeve 74, and a control rod, not shown, has an end abutting flange 72 and an end extending within housing 52 to control a slit diaphragm assembly, not shown.

The light beam provided by the lamp passes through the slit formed by the slit diaphragm assembly and through an optical system in the illumination column 50 to be deflected by mirror 54 toward the eye of a patient. The optical system includes a filter assembly operable by a lever 76 to selectively position one of a plurality of filters in the path of the light beam, such filters including a normal light filter, a heat absorption filter, a 50% density filter, a blue-green cobalt filter and any other desired filters. The optical system also includes an aperture assembly operated by a lever 78 to position an aperture of selected size in the path of the light beam, such apertures desirably having sizes of 0.2 mm, 1 mm, 3 mm, 4 mm, 6 mm, 8 mm and 10 mm. The optical system can be rotated to vertically or horizontally orient the slit image.

With the exception of the combination control device 64, the above described structure of the slit lamp is conventional; and, thus, a detailed description thereof has been omitted. However, reference is made to the MENTOR Slit Lamp produced by Mentor Division of Codman & Shurtleff, Inc. and accompanying literature for more detailed structural and operational information relative to the above described structure and further reference is made to patent application Ser. No. 373,335 filed June 25, 1973 for more detailed discussion of the structure and operation of the combination control device 64 and the illumination column 50.

The microscope 46 is of the steroscopic binocular type; however, while such microscopes are preferred for use with slit lamps due to the stereoscopic effect provided by the separate converging light paths therethrough, the photographic apparatus of the present invention can be utilized with monobjective binocular microscopes or any other desired type of microscope, it being preferred that the microscope be of the binocular type to permit viewing of the object through one ocular while a photograph is taken through the other ocular, as will be described in more detail hereinafter. Microscope 46, as best shown in FIGS. 2, 3 and 4, has a body 80 mounted on an arcuate end of microscope arm 44 and supporting at one end a pair of housings 82 and 84 slidably mounting oculars 86 and 88, respectively, the housings 82 and 84 each having a rotatable ring 85 for axially focusing the microscope. At the other end of body 80 are a pair of horizontally aligned objectives 90 and 92 and a pair of vertically aligned objectives 94 and 96, the objectives being mounted on a plate 98 which is rotatable 90° under the control of a lever 100 such that the objectives 94 and 96 can be substituted for the objectives 90 and 92, respectively. A shield 101 extends from body 80 to house the objectives and has a cylindrical portion 102 terminating at a frusto-conical portion 103 having an open end.

The structure and operation of the binocular microscope 46 is conventional; and, thus, the specific details of the optics of the microscope will not be further set forth, it being noted, for example, that the objectives 90 and 92 can be 1X and the objectives 94 and 96 can be 1.6X while the oculars 86 and 88 can include interchangeable 10X and 16X eye pieces such that total magnifications of 10X, 16X and 25.6X can be obtained with various combinations of the oculars and objectives.

In accordance with the present invention, photographic apparatus is mounted on the microscope 46 to permit photographs of an eye under examination to be taken through one of the oculars of the microscope, the photographic apparatus including a 35 mm photographic camera 104 having a lens assembly 106 mounted in an internally threaded barrel 108 to be axially movable by a focus ring 110. An electronic exposure control mechanism 112 is disposed adjacent the lens 106 to automatically control shutter speed and lens aperture in accordance with light conditions, and the shutter is operated by a shutter release button 114 on the top of the camera via a remote operator 116. As thus far described, the camera 104 is conventional, and any automatic photographic camera can be used with the present invention, for example, Model 35 EC2 of Olympus Optical Co., Ltd., Tokyo, Japan, it being noted that either or both shutter speed and aperture can be controlled to provide semi- or fully automatic operation.

The photographic camera 104 is modified in accordance with the present invention to remove the light sensor normally mounted on the front face of the camera at 118 and to connect the electronic exposure control mechanism 112 with a socket terminal 120 by a pair of wires indicated diagrammatically at 122. The windows at 118, the normal position of the light sensor, and at a view finder 124 can be covered or blocked in that the light sensor has been removed and the viewfinder 124 is not required for operation.

Figure 6:
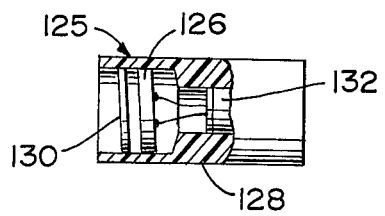
FIG. 6 is a broken section of the light sensor of the photographic apparatus of the present invention.

The light sensor is generally indicated at 125 and, as best shown in FIG. 6, includes a cadmium sulphide (CdS) photoelectric cell 126 mounted in a housing 128, and a neutral-density filter 130 is mounted in front of the photoelectric cell 126, the filter 130 being, for example, a Wratten 0.3 density filter to provide 50% light transmission therethrough. The light sensor housing 128 has a socket terminal 132 connected with the photoelectric cell 126, and a coaxial cable 134 has plug terminals 136 and 138 on opposite ends thereof to be received in socket terminals 120 and 132, respectively, thereby electrically connecting the photoelectric cell 126 with the electronic exposure control mechanism 112. The light sensor housing 128 is secured in any suitable manner, such as by cement 140, to the outer surface of an annular collar 142 having a set screw 144 extending therethrough, and the collar 142 has a size to extend around the cylindrical portion 102 of the objective shield 101 with the set screw 144 holding the collar in place. The photoelectric cell 126 is oriented at an angle to the observation axis of the microscope such that the central axis of the photoelectric cell intersects the observation axis of the microscope at the eye of the patient.

Figure 5:
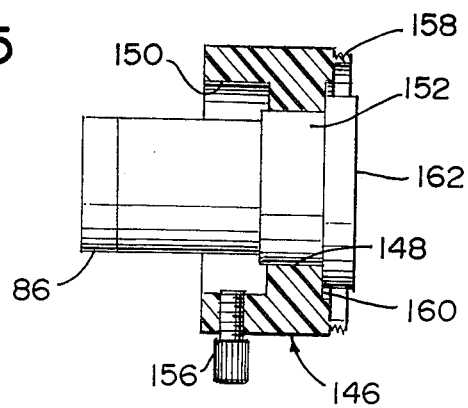
FIG. 5 is a cross section of the assembled adapter ring and ocular of the photographic apparatus of the present invention.

The photographic camera 104 is mounted on the microscope 46 by an adapter ring 146, as best shown in FIGS. 2, 3 and 5, having a small central bore 148 therethrough and a counterbore 150, the diameter of bore 148 corresponding to the diameter of an annular shoulder 152 of ocular 86 and the diameter of bore 150 corresponding to the outer diameter of an end 154 of ocular housing 82. A set screw 156 extends into bore 150 to hold the adapter ring 146 on the end 154 of the ocular housing and prevent rotation of the adapter ring, and an externally threaded wall 158 extends from the end of adapter ring 146 to threadedly engage the internally threaded portion of barrel 108 of the photographic camera 104. The adapter ring 146 has an annular recess 160 adjacent wall 158 for receiving a rim 162 of the ocular 86.

It is preferred to supply an additional ocular for mounting in the adaptor ring 146 such that the adapter ring and the ocular can remain mounted on the photographic camera to facilitate attachment of the camera to the microscope; however, if desired, one of the oculars of the microscope can be removed therefrom for mounting on the adapter ring 146 each time a photograph is to be taken. When it is desired to change the magnification of the microscope by changing oculars, the previously used ocular can be disassembled from the adapter ring and the new ocular substituted therefor.

In use, the collar 142 is installed on the objective shield 102 by tightening the set screw 144 with the light sensor 125 at any desired rotational position around the shield, and the collar is preferably left in place during normal use of the slit lamp to examine the eyes of patients. When it is desired to photograph an eye of a patient, one of the oculars of the microscope 46 is removed, and the ocular attached to the camera by adapter ring 146 is inserted into the end 154 of the ocular housing with the set screw 156 being tightened to engage the end 154 of the ocular housing. The cable 134 is now plugged into terminals 120 and 132; and, in order to photograph the eye, the opthalmologist merely views the eye through the other ocular and actuates the shutter release button 114 via the remote operator 116 to expose the film in the camera.

The Cds photoelectric cell 126, as is well known, is responsive to light to decrease its resistance; and, thus, the resistance of the photoelectric cell 126 represents a signal supplied to the electronic exposure control mechanism 112 to automatically set the shutter speed and lens aperture for each photograph. The rim 162 of the ocular is seated against the camera lens assembly 106 when the adapter ring 146 is screwed onto the barrel 108 of the camera; and, accordingly, the focus of the camera 104 cannot be altered once the adapter ring and ocular are mounted thereon. Thus, the opthalmologist is not required to make any adjustments of the camera and is free to concentrate on the patient. In order to assure that the camera is level when a photograph is taken, a bubble level 164 can be inserted in the accessory shoe normally provided on the camera for mounting a flash unit.

Since the opthalmologist is able to view the eye of the patient through the unoccupied ocular of the microscope, a series of photographs can be taken in quick succession by merely respositioning the slit beam and the microscope as desired while continuously viewing the eye.

Figure 8:
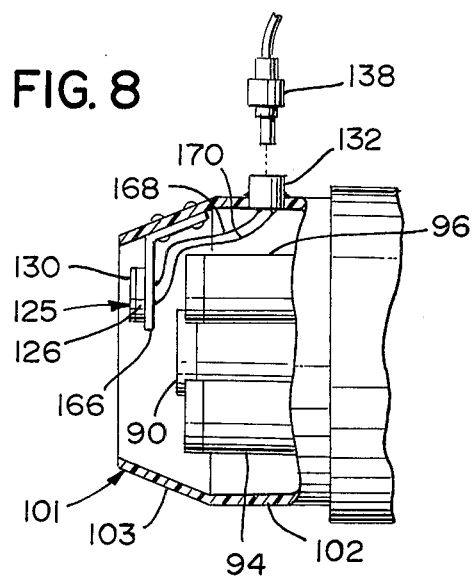
FIG. 8 is a section taken along line 8—8 of FIG. 7.

A modification of the support for the light sensor 125 is shown in FIGS. 7 and 8, wherein the light sensor is mounted on a leg of a bracket 166 secured, such as by rivets, to the conical portion 103 of the shield 101. The socket terminal 132 is supported on the cylindrical portion 102 of the shield 101 and is connected with the photoelectric cell 125 via wires 168 and 170. The light sensor 125 is disposed equidistant from the horizontally aligned objectives and is vertically offset from the observation axis plane of the converging light paths of the microscope; and, in this position, the light sensor does not interfere with the objectives since only the horizontally aligned pair of objectives are operative.

With the light sensor 125 positioned adjacent the objectives of the microscope either supported on collar 142 or directly on shield 101, all desired structures of the human eye can be photographed including the external portions such as skin, eyelashes, the puncti and the conjunctiva; the anterior segment such as the cornea, the iris, the pupil, the front portion of the lens and the anterior chamber; the entire lens; and the posterior segment such as the structure behind the lens, the vitreous body, the optic nerve, supporting structures, the fundi and the retina. The equidistant positioning of the light sensor 125 within the objective shield 101, as shown in FIGS. 7 and 8, is particularly effective for obtaining photographs of the fundi.

Figure 9:
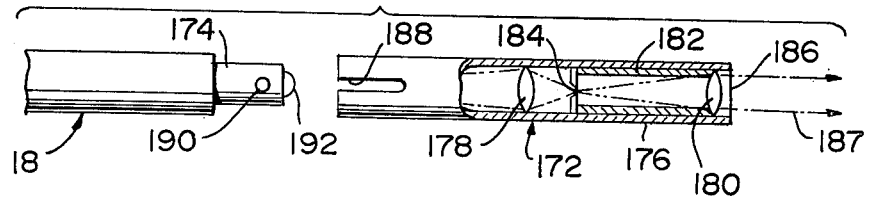
FIG. 9 is an exploded view of an adapter for the fixation light of the slit lamp in accordance with the present invention.

While the photographic apparatus of the present invention provides clear and accurate photographs utilizing only the slit light beam, background illumination for the eye to provide a reference for the slit light beam can be provided in accordance with the present invention without requiring an additional light source by utilizing the fixation light 18. To this end, a fixation light adapter 172, as shown in FIG. 9, is provided in accordance with the present invention, the fixation light adapter being designed to be attached to a lamp housing 174 of the fixation light 18. The fixation light adapter 172 is formed of an open ended tube 176 having a pair of condensers 178 and 180 disposed therein in axially spaced relation. A cylindrical member 182 is disposed between the condensers to act as a spacer and has an aperture 184 in the end adjacent condenser 178 such that collimated light 187 is directed from an open end 186 of the tube 176. The opposite end of tube 176 has an axially extending slot 188 therein adapted to accomodate a dimple 190 on the fixation lamp housing 174. The tube 176 receives the lamp housing 174 with a sliding friction fit such that the fixation light adapter 172 can be longitudinally positioned to vary the spacing between condenser 178 and a fixation lamp 192 supported in housing 174 and thereby permit light intensity adjustment.

Figure 10:
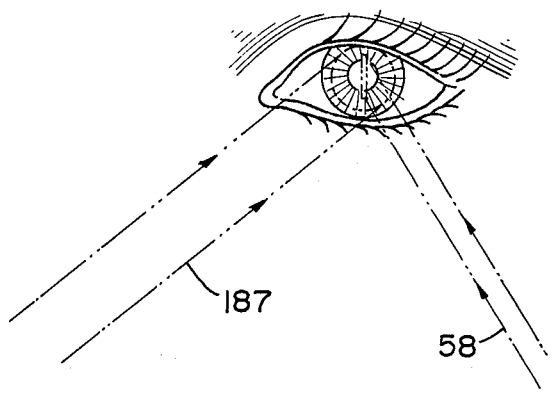
FIG. 10 is a diagrammatic illustration of a slit light beam and background illumination directed to an eye being examined.

The cross sectional dimension of the background light beam 187 is substantially the same as the maximum dimension of the slit light beam 58; and, as shown in FIG. 10, the light beam 187 provides background reference illumination for the slit light beam 58 to render the photographs clearer.

When an Olympus Model 35 EC2 camera is used with the present invention, the wires leading to the photoelectric cell are rerouted to the flash terminal on the side of the camera, the flash system wires are disconnected and the photoelectric cell is removed to be positioned adjacent the objectives of the microscope. The camera preferably uses high speed film, such a Kodak high speed Ektachrome film (tungsten 3200K); and, when this film is used, the neutral-density filter 130 in the light sensor 125 is preferably a Wratten 0.3 density, neutral-density filter having a 50% light transmission characteristic. Of course, the light transmission characteristic of the neutral-density filter 130 is dependent on the speed of the film utilized. In order to increase the speed of the Kodak high speed Ektachrome film, it is preferred to use Kodak Special Processing which increases the film speed 2½ times to ASA320.

The positioning of the light sensor adjacent the objective is particularly advantageous due to the wide variety of photographs of the eye that can be taken when light is sensed along the observation axis, as mentioned above, the camera using the optical system of one of the oculars of the microscope with no light from the optical system required for the light sensor, and the obtention of proper light exposure in accordance with the image at the objective. Furthermore, with the light sensor equidistant between the objectives and the angle oriented such that the central axis intersects the point of convergence of the light paths of the microscope, accurate fundi photographs are obtained since the angle of light reflected from the retina is small and extremely critical in fundi photographing. While it is preferred to position the photoelectric cell adjacent the objectives of the microscope, fiber optics could be utilized to collect light adjacent the objectives of the microscope and transmit the light as a signal to a photoelectric cell on the camera to provide automatic exposure operation.

The adapter 146 provides the function of supporting and centering the ocular, mounting the camera on the microscope and immobilizing the focusing mechanism of the camera, and the postioning of the camera abutting the ocular permits the camera lens to collect light through the ocular while light reduction is provided independent of the optics of the camera. With the camera mounted on the microscope in this manner, the camera is focused as the microscope is focused to further simplify the photographing operation.

Inasmuch as the present invention is subject to many variations, modifications and changes in detail, it is intended that all subject matter described above or shown in the accompanying drawings be interpreted as illustrative and not in a limiting sense.

What is claimed is:

1. In combination with an opthalmic slit lamp device having a binocular microscope, an apparatus for photographing an object through said microscope, comprising:

photographic camera means having an automatic exposure control mechanism and a focusing lens;
   adapter means for mounting said photographic camera means on the ocular of the microscope, wherein said camera means is supported before said ocular via its focusing lens;
   light sensing means for providing a signal representative of light sensed thereby;
   means for coupling said signal from said light sensing means to said automatic exposure control mechanism to control operation thereof; and
   mounting means for positioning said light sensing means adjacent the objective of the microscope whereby said automatic exposure control mechanism is operated in response to light at the objective of the microscope while the image to be photographed is transmitted through the microscope to said photographic camera means.

2. Apparatus as recited in claim 1 wherein said light sensing means includes a photoelectric cell and a neutral-density filter disposed adjacent said photoelectric cell to reduce light transmitted to said photoelectric cell.

3. Apparatus as recited in claim 2 wherein said mounting means for positioning said light sensing means includes a collar adapted to be removably attached to said microscope, said photoelectric cell being mounted on said collar at an angle to the central axis thereof whereby the central axis of said photoelectric cell is adapted to intersect the observation axis of the microscope at the object to be photographed.

4. Apparatus as recited in claim 2 wherein said photographic camera means has a terminal electrically connected with said automatic exposure control mechanism, said light sensing means has a terminal electrically connected with said photoelectric cell and said coupling means includes a cable having terminal at opposite ends thereof removably connected with said photographic camera means terminal and said light sensing means terminal.

5. Apparatus as recited in claim 1 wherein said photographic camera means has a lens assembly axially movable in a threaded barrel for focusing, and said adapter means includes a threaded adapter ring having a central bore therethrough for receiving the ocular, said adapter ring being adapted to threadedly engage said barrel to seat the end of the ocular against said lens assembly to prevent axial focusing movement thereof.

6. Apparatus for photographing an enlarged image of an object comprising
   a binocular microscope including first and second oculars and objective means associated with said first and second oculars to produce an enlarged image thereat;
   a photographic camera having an automatic exposure control mechanism, a lens assembly and a barrel surrounding said lens assembly;
   an adapter ring having a central bore receiving said first ocular, said adapter ring being secured to said barrel to align said first ocular with said lens assembly and mount said photographic camera on said microscope; and
   light sensing means disposed adjacent said objective means of said microscope for sensing light at said objective means and providing a signal representative of the sensed light to said automatic exposure control mechanism whereby said automatic exposure control mechanism is operated in response to light at said objective means and the image to be photographed is transmitted to said photographic camera through said first ocular while the image to be photographed can be viewed through said second ocular.

7. Apparatus as recited in claim 6 wherein said light sensing means includes a photoelectric cell and a neutral-density filter positioned to reduce light transmitted to said photoelectric cell.

8. Apparatus as recited in claim 6 wherein said objective means includes first and second objectives cooperating with said first and second oculars to define converging light paths and said light sensing means includes a photoelectric cell disposed equidistant from said first and second objectives.

9. Apparatus as recited in claim 8 wherein said converging light paths define an observation axis plane and said photoelectric cell is offset from said observation axis plane and angularly oriented such that the central axis of said photoelectric cell intersects said converging light paths at the point of convergence thereof.

10. Apparatus as recited in claim 9 wherein said microscope includes a shield surrounding said first and second objectives and further comprising bracket means mounted on said shield for supporting said photoelectric cell within said shield.

11. Apparatus as recited in claim 9 wherein said microscope includes a shield surrounding said first and second objectives and further comprising a collar removably mounted on said shield for supporting said photoelectric cell.

12. Apparatus as recited in claim 6 wherein said microscope includes a shield surrounding said objective means and further comprising means removably and rotatably mounted on said shield to support said light sensing means.

13. Apparatus as recited in claim 12 wherein said objective means defines an observation axis and said light sensing means includes a photoelectric cell angularly oriented such that the central axis of the photoelectric cell intersects the observation axis at the object to be photographed.

14. Apparatus as recited in claim 6 wherein said photographic camera has a terminal electrically connected with said automatic exposure control mechanism and said light sensing means includes a photoelectric cell electrically connected with a terminal and a cable having terminals at opposite ends thereof removably connected with said photographic camera terminal and said photoelectric cell terminal.

15. A slit lamp comprising:
   pivotally mounted slit illumination means for projecting a slit light beam toward an eye of a patient;
   a pivotally mounted binocular microscope having a first ocular and a first objective defining a first light path and a second ocular and a second objective defining a second light path converging with said first light path at the eye of the patient;
   a photographic camera mounted on said first ocular via said camera lens and having an automatic exposure control mechanism; and
   light sensing means including a photoelectric cell positioned adjacent said first and second objectives and means for electrically coupling said photoelectric cell with said automatic exposure control mechanism whereby said automatic exposure control mechanism is operated in response to light at said first and second objectives and the image of the eye to be photographed is transmitted to said photographic camera along said first light path while the image of the eye can be viewed along said second light path to permit movement of said slit illumination means and said binocular microscope for successive photographs during continuous viewing of the eye.

16. A slit lamp as recited in claim 15 and further comprising a pivotally mounted fixation light and an adapter associated with said fixation light including condenser means for forming a collimated light beam adapted to be directed toward the eye of the patient to provide background illumination.

17. A slit lamp as recited in claim 16 wherein said fixation light has a housing supporting a fixation lamp and said adapter is mounted on said housing to be axially slidable therealong to adjust the intensity of said collimated light beam.

18. A slit lamp as recited in claim 17 wherein said adapter includes a tube having an open end receiving said fixation light housing, a pair of axially spaced condensers disposed in said tube and a spacer separating said condensers and forming an aperture adjacent one of said condensers.

19. A slit lamp as recited in claim 15 wherein said binocular microscope includes a shield surrounding said first and second objectives and further comprising means mounting said photoelectric cell on said shield angularly oriented such that the central axis of said photoelectric cell intersects said first and second light paths at the eye of the patient.

20. A slit lamp as recited in claim 15 wherein said light sensing means includes a neutral density filter for reducing light transmission to said photoelectric cell.

* * * * *

UNITED STATES PATENT AND TRADEMARK OFFICE
CERTIFICATE OF CORRECTION

PATENT NO. : 3,944,342
DATED : March 16, 1976
INVENTOR(S) : Martinez, Miquel

It is certified that error appears in the above-identified patent and that said Letters Patent are hereby corrected as shown below:

In Column 6, Line 41, the word "Cds" should read --- CdS ---.

In Column 6, Line 61, the word "respositioning" should read --- repositioning ---.

In Column 7, Line 61, the word "such a" should read --- such as ---.

In Column 9, Line 14, the word "terminal" should read --- terminals ---.

Signed and Sealed this

Sixteenth Day of November 1976

[SEAL]

Attest:

RUTH C. MASON
*Attesting Officer*

C. MARSHALL DANN
*Commissioner of Patents and Trademarks*